United States Patent
Desai et al.

(10) Patent No.: US 7,135,193 B2
(45) Date of Patent: *Nov. 14, 2006

(54) LIPOSOME COMPOSITIONS OF PORPHYRIN PHOTOSENSITIZERS

(75) Inventors: Narendra R. Desai, Danbury, CT (US); Bushra J. Agha, Durham, NC (US); Kalidas Madhavrao Kale, Harriman, NY (US); James R. Lawter, Goshen, NY (US)

(73) Assignee: QLT, Inc., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 11/020,462

(22) Filed: Dec. 22, 2004

(65) Prior Publication Data

US 2005/0107329 A1 May 19, 2005

Related U.S. Application Data

(63) Continuation of application No. 09/589,358, filed on Jun. 8, 2000, now Pat. No. 6,890,555, which is a continuation of application No. 08/489,850, filed on Jun. 13, 1995, now Pat. No. 6,074,666, which is a continuation of application No. 07/832,542, filed on Feb. 5, 1992, now abandoned.

(51) Int. Cl.
*A61K 9/127* (2006.01)

(52) U.S. Cl. ...................... 424/450; 514/410

(58) Field of Classification Search ................ 424/450, 424/1.21, 9.521, 9.61, 9.51; 514/410; 425/450
See application file for complete search history.

(56) References Cited

U.S. PATENT DOCUMENTS

| | | | |
|---|---|---|---|
| 4,755,388 A | 7/1988 | Heath | |
| 4,776,991 A | 10/1988 | Farmer | |
| 4,797,285 A | 1/1989 | Barenholz | |
| 4,857,319 A | 8/1989 | Crowe | |
| 4,880,635 A | 11/1989 | Janoff | |
| 4,882,165 A | 11/1989 | Hunt | |
| 4,913,907 A | 4/1990 | Jori | |
| 4,920,143 A | 4/1990 | Levy | |
| 5,010,073 A | 4/1991 | Kappas | |
| 5,270,053 A | 12/1993 | Schneider | |
| 5,277,913 A | 1/1994 | Thompson | |
| 5,389,378 A | 2/1995 | Madden | |
| 5,705,518 A | 1/1998 | Richter | |
| 5,707,608 A * | 1/1998 | Liu | ......................... 424/9.61 |
| 6,074,666 A | 6/2000 | Desai | |
| 6,207,456 B1 | 3/2001 | Baru | |
| 6,265,387 B1 | 7/2001 | Wolff | |

FOREIGN PATENT DOCUMENTS

| | | |
|---|---|---|
| CA | 2047969 | 2/1992 |
| EP | 0451103 | 9/1991 |
| GB | 2256139 | 2/1992 |
| WO | WO-94/11100 | 5/1994 |

OTHER PUBLICATIONS

Barel et al., (1986) Med Biol Environ 14(1):35-40.

(Continued)

*Primary Examiner*—Gollamudi S. Kishore
(74) *Attorney, Agent, or Firm*—Morrision & Foerster LLP

(57) ABSTRACT

Liposomal pharmaceutical formulations incorporating porphyrin photosensitizers useful for photodynamic therapy or diagnosis of malignant cells. The liposomal formulations comprise a porphyrin photosensitizer, particularly the hydro-mono benzoporphyrins (BPD) having light absorption maxima in the range of 670–780 nanometers, a disaccharide or polysaccharide and one or more phospholipids.

26 Claims, 4 Drawing Sheets

OTHER PUBLICATIONS

Cohen et al., (1986) Arch Biochem & Biophys 247:57-61.
Cozzani et al., (1985) Chem Biol Interact 53(1-2):131-143.
Cozzani et al., (1986) Med Biol Environ 14(1):73-76.
Cuomo et al., (1990) Br J Cancer 62:966-970.
Davis et al., (1990) Laryngoscop 100(7):682-686.
Facchini et al., (1984) Med Biol Environ 12(1):469-474.
Firey et al., (1988) Photochemistry and Photobiology 48:357-360.
Gantchev et al., (1989) Studia Biophysica 131:7-20.
Grossweiner, (1985) Adv Exp Med Biol 193:181-192.
Grossweiner, (1987) Proc SPIE-Int Soc Opt Eng 712:149-153.
Johnson et al., (1990) Photodynamic Therapy: Mechanisms II, SPIE:266-280.
Kuzelova et al., Biochemistry (1995) 34:11245-11255.
Love et al., Liposomes in Drug Delivery, Gregoriadis et al., (eds.), (1993) pp. 149-188.
Margalit et al., (1985) Adv Exp Med Biol 193:303-311.
Milanesi et al., (1989) Int J Radiat Biol 55:59-69.
Milanesi et al., (1990) Br J Cancer 61:846-850.
Morgan et al., (1988) Proc SPIE-Int Soc Opt Eng 847:180-196.
Oku et al., Biol. Pharm. Bull. (1997) 20:670-673.
Parasassi et al., (1989) Inorganica Chemica Acta 66:137-139.
Poretz et al., (1989) Proc SPIE-Int Soc Opt Eng 1065:197-203.
Ricchelli et al., (1985) F.E.C.S. Int Conf Chem Biotechnol Act Nat Prod., [Proc.] 3rd, 5:241-244.
Ricchelli et al., (1987) New Directions in Photodunamic Therapy, SPIE 847:101-106.
Ricchelli et al., (1988) Proc SPIE-Int Soc Opt Eng 847:101-106.
Ricchelli et al., J. of Photochemistry and Photobiology (1995) 29:65-70.
Richter et al., Photochemistry and Photobiology (1993) 57:1000-1006.
Scherphof et al., Biochimica et Biophysica Acta (1979) 556:196-207.
Spikes, (1983) Adv Exp Med Biol 160:181-192.
Sucio et al., (1988) NATO ASI Ser., Ser. H, 15 (Photosensibilization) 431-433.
Thomas et al., (1988) Biochim et Biophys Acta 962:297-307.
Zhou et al., (1988) Photochemistry and Photobiology 48:487-492.

* cited by examiner

BPD-DA

BPD-DB

BPD-MA and

BPD-MB

LIPOSOME COMPOSITIONS OF PORPHYRIN PHOTOSENSITIZERS

CROSS-REFERENCE TO RELATED APPLICATIONS

This application is Continuation of U.S. Ser. No. 09/589,358 filed Jun. 8, 2000 now U.S. Pat. No. 6,890,555, which is a Continuation of U.S. Ser. No. 08/489,850 now U.S. Pat. No. 6,074,666 filed Jun. 13, 1995, which is a Continuation of U.S. Ser. No. 07/832,542 filed Feb. 5, 1992, abandoned. The contents of these documents are incorporated herein by reference.

FIELD OF THE INVENTION

The invention relates to improved pharmaceutical formulations comprising liposomes incorporating porphyrin photosensitizers. Specifically, the invention is directed to a freeze-dried pharmaceutical formulation comprised of a porphyrin photosensitizer, a disaccharide or polysaccharide and one or more phospholipids which, upon reconstitution with a suitable aqueous vehicle, forms liposomes containing the porphyrin photosensitizer. Particular porphyrin photosensitizers which are advantageously employed in the practice of this invention include the hydro-monobenzoporphyrins having a light absorption maxima in the range of 670–780 nanometers. The photosensitizing formulations are useful to mediate the destruction of unwanted cells or tissues or other undesirable materials by irradiation or to detect their presence through flourescence.

DESCRIPTION OF THE RELATED ART

The use of porphyrin compounds, and in particular hematoporphyrin and hematoporphyrin derivative (HPD), have been known for some time to be useful systemically when combined with light, for the treatment and diagnosis of malignant cells. The porphyrins appear to naturally "localize" in malignant tissue where they absorb light at certain wavelengths when irradiated, providing a means to detect the tumor by the location of the fluorescence. Accordingly, preparations containing the porphyrins are useful in the diagnosis and detection of such tumor tissues. (See, e.g. "Porphyrin Photosensitization", Kessel, D., et al., eds. (1983) Plenum Press). In addition, the porphyrins also have the capability of exhibiting a cytotoxic effect on the cells or other tissues in which they are localized when exposed to light at the appropriate wavelength. (See, e.g., Diamond, I., et al., *Lancet* (1972) 2: 1175–1177; Dougherty, T. J. et al., "The Science of Photo Medicine" (1982) J. D. Regan & J. A. Parrish, eds., pp. 625–638; Dougherty, T. J., et al., "Cancer: Principles and Practice of Oncology" (1982) V. T. DeVita Jr., et al., eds., pp. 1836–1844). It has been postulated that the cytotoxic effect of the porphyrins is due to the formation of singlet oxygen when exposed to light (Weishaupt, K. R., et al., *Cancer Research*, (1976) 36: 2326–2329). The successful treatment of AIDS-related oral Kaposi's Sarcoma with a purified form of HPD, Photofrin® porfimerسodium, was described in Schwietzer, V. G. et al., *Otolaryngology—Head and Neck Surgery* (1990) 102: 639–649.

In addition to systemic use for the treatment and diagnosis of tumors, the porphyrins can be used in a variety of other therapeutic applications. For example, photosensitizers are useful in the detection and treatment of artherosclerotic plaques as disclosed in U.S. Pat. Nos. 4,517,762 and 4,577,636. U.S. Pat. Nos. 4,500,507 and 4,485,806 describe the use of radiolabeled porphyrin compounds for tumor imaging. Porphyrin compounds have also been used topically to treat various skin diseases as disclosed in U.S. Pat. No. 4,753,958.

A number of porphyrin photosensitizer preparations have been disclosed for therapeutic applications. A photosensitizer preparation widely used in the early stages of photodynamic therapy both for detection and treatment was a crude derivative of hematoporphyrin, also called hematoporphyrin derivative (HPD) or Lipson derivative, prepared as described by Lipson et al., J. Natl. Cancer Inst. (1961) 26: 1–8. A purified form of the active component(s) of HPD was prepared by Dougherty and co-workers by adjustment of the pH to cause aggregation and recovery of the aggregate, as disclosed in U.S. Pat. Nos. 4,649,151, 4,866,168, 4,889,129 and 4,932,934. A purified form of this product is used clinically under the trademark Photofrin® porfimer sodium. Of particular interest in the context of the present invention are a group of modified porphyrins, known as "green porphyrins" (Gp), having a light absorption maximum between 670–780 nm which have been shown to confer cytotoxicity to target cells at concentrations lower than those required for hematoporphyrin or HPD. These Gp are obtained using Diels-Alder reactions of acetylene derivatives with protoporphyrin under appropriate conditions. The preferred forms of Gp are the hydro-monobenzoporphyrin derivatives ("BPD"). The preparation and use of the Gp and BPD compounds are disclosed in U.S. Pat. No. 4,920,143 and U.S. Pat. No. 4,883,790, hereby incorporated by reference into the disclosure of the present application.

While the porphyrin compounds naturally have the ability to localize in neoplastic tissue while being cleared from the normal surrounding tissue, the selectivity of the porphyrin sensitizers is somewhat limited. Because tumor tissues generally include various components such as malignant cells, the vascular system, macrophages, fibroblasts, etc., the distribution of the photosensitizer in the tissue may be highly heterogeneous, especially for those photosensitizers which are not homogeneous and contain a mixture of components with different degrees of hydro or lipo-solubility. Zhou, C. et al., *Photochemistry and Photobiology*, (1988) 48: 487–492. The low selectivity of some of these tumors as tumor localizers may lead to side effects such as hypersensitivity exhibited nonspecifically throughout the organism. Therefore, an active area of research is to increase the tumor selectivity of known porphyrin photosensitizers and to identify those porphyrin photosensitizers which exhibit higher tumor-selectivity. In general, those photosensitizers which are more lipophilic tend to exhibit greater tumor targeting. J. D. Spikes, et al., *Lasers in Medical Science*, (1986) 2: 3, 3–15.

It has recently been shown that the encapsulation of certain drugs in liposomes before administration has a marked effect on the pharmoco-kinetics, tissue distribution, metabolism and efficacy of the therapeutic agent. Liposomes are completely closed lipid bilayer membranes containing an entrapped aqueous volume which are formed spontaneously on addition of an aqueous solution to a dry lipid film. They may be unilamellar vesicles possessing a single membrane bilayer or multilamellar vesicles having multiple membrane bilayers, each separated from the next by an aqueous layer. The bilayer is composed of two lipid monolayers having a hydrophobic "tail" region and a hydrophilic "head" region. The structure of the membrane bilayer is such that the hydrophobic (non polar) "tails" of the lipid monolayers orient towards the center of the bilayer while the hydrophilic "heads" orient toward the aqueous phase.

In a liposome-drug delivery system, a hydrophilic therapeutic agent is entrapped in the aqueous phase of the liposome and then administered to the patient. Alternatively, if the therapeutic agent is lipophilic, it may associate with the lipid bilayer. Liposomes may be used to help "target" a drug to the active site or to solubilize hydrophobic drugs for administration.

In an effort to increase the tumor selectivity of porphyrin photosensitizers, the porphyrin compounds have been incorporated into unilamellar liposomes resulting in a larger accumulation and more prolonged retention of the photosensitizer by both cultured malignant cells and experimental tumors in vivo. Jori et al., *Br. J. Cancer*, (1983) 48: 307–309; Cozzani et al., *In Porphyrins in Tumor Phototherapy*, Andreoni et al., eds., (1984) pp. 177–183, Plenum Press. The more efficient targeting of tumor tissues by liposome-associated porphyrins may be partly due to the specific delivery of the phospholipid vesicles to serum lipoproteins, which have been shown to interact preferentially with hyperproliferative tissue such as tumors through receptor mediated endocytosis. In this manner the selectivity of porphyrin uptake by tumors is increased as compared with photosensitizers dissolved in aqueous solution. See Zhou et al., supra.

Accordingly, hematoporphyrin and hematoporphyrin dimethylester have been formulated in unilamellar vesicles of dipalmitoyl-phosphatidyl choline (DPPC) and liposomes of dimyristoyl (DMPC) and distearoyl-phosphatidyl choline (DSPC). Zhou et al., supra; Ricchelli, F., *New Directions in Photodynamic Therapy*, (1987) 847: 101–106; Milanesi, C., *Int. J. Radiat. Biol.*, (1989) 55: 59–69. Similarly, HP, Photofrin® porfimer sodium, and tetrabenzo-porphyrins have been formulated in liposomes composed of egg phosphatidyl choline (EPC). Johnson, F. M. et., *Proc. Photodynamic Therapy: Mechanisms II*, (1990), Proc. SPIE-Int. Soc. Opt. Eng., 1203: 266–80.

Due to the importance of photodynamic therapy in the treatment of cancer, there is a continuing need to identify new photosensitizer formulations that are stable, exhibit ease in manufacturing and which selectively deliver the photosensitizer, particularly the more hydrophobic photosensitizers, to the target tissue in an efficient manner.

SUMMARY OF THE INVENTION

The present invention involves a freeze dried pharmaceutical formulation comprising a porphyrin photosensitizer, a disaccharide or polysaccharide, and one or more phospholipids, which freeze-dried formulation forms liposomes containing a therapeutically effective amount of the porphyrin photosensitizer upon reconstitution with a suitable aqueous vehicle. The invention also relates to the liposome composition formed upon reconstitution with said aqueous vehicle.

The porphyrin photosensitizers usable in the practice of this invention include any of the known porphyrin derivative compounds useful in photodynamic therapy characterized in that they contain a porphyrin ring system. These include deuteroporphyrin, etioporphyrin, protoporphyrin, hematoporphyrin, pheophorbide and derivatives thereof. Particularly useful are hematoporphyrin and derivatives thereof as described in U.S. Pat. Nos. 4,649,151, 4,866,168, 4,889,129 and 4,922,934. The most preferred porphyrin photosensitizers usable in the present invention are the (Gp) having a light absorption maximum between 670–780 nm wherein the Gp is selected from the group consisting of those compounds having the formulae set forth in FIG. 1 and mixtures thereof and the metalated and labeled forms thereof;

wherein each $R^1$ and $R^2$ is independently selected from the group consisting of carbalkoxy (2–6C), alkyl (1–6C) sulfonyl, aryl (6–10C) sulfonyl, aryl (6–10C); cyano; and —$CONR^5CO$— wherein $R^5$ is aryl (6–10C) or alkyl (1–6C);

each $R^3$ is independently carboxyalkyl (2–6C) or a salt, amide, ester or acylhydrazone thereof, or is alkyl (1–6C); and $R^4$ is $CHCH_2$, $CHOR^{4'}$, —CHO, —$COOR^{4'}$, $CH(OR^{4'})CH_3$, $CH(OR^{4'})CH_2OR^{4'}$, —$CH(SR^{4'})CH_3$, —$CH(NR^{4'}_2)CH_3$, —$CH(CN)CH_3$, —$CH(COOR^{4'})CH_3$, —$CH(OOCR^{4'})CH_3$, —$CH(halo)CH_3$, or —$CH(halo)CH_2(halo)$, wherein $R^{4'}$, is H, alkyl (1–6C) optionally substituted with a hydrophilic substituent, or wherein $R^4$ is an organic group of <12C resulting from direct or indirect derivatization of vinyl, or wherein $R^4$ consists of 1–3 tetrapyrrole-type nuclei of the formula —L—P wherein —L— is selected from the group consisting of

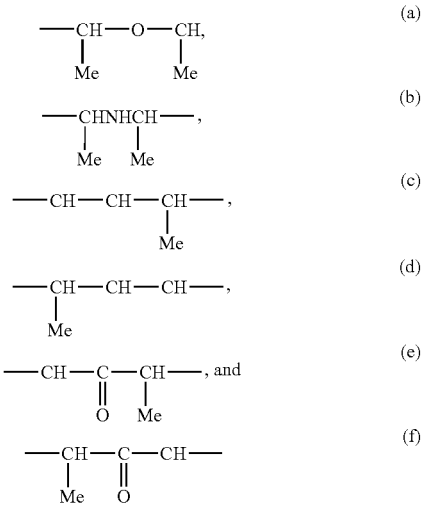

and P is selected from the group consisting of Gp which is of the formula 1–6 but lacking $R^4$ and conjugated through the position shown as occupied by $R^4$ to L, and a porphyrin of the formula:

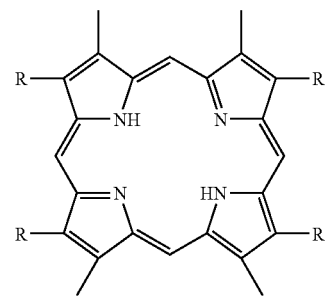

wherein each R is independently H or lower alkyl (1–4C);

wherein two of the bonds shown as unoccupied on adjacent rings are joined to $R^3$ and one of the remaining bonds shown as unoccupied is joined to $R^4$ and the other to L;

with the proviso that if $R^4$ is $CHCH_2$, both $R^3$ cannot be carbalkoxyethyl.

The preparation and use of such compounds is disclosed in U.S. Pat. Nos. 4,920,143, and 4,883,790 hereby incorporated by reference. The most preferred compounds of the hydro-monobenzoporphyrins recited above are the compounds of formulas 3 and 4 designated benzoporphyrin derivative (BPD) which have the formulas set forth in FIG. 2. These are hydrolyzed or partially hydrolyzed forms of the rearranged products of formula 3 or 4, wherein one or both of the protected carboxyl groups of $R^3$ are hydrolyzed. Particularly preferred is the compound referred to as BPD-MA in FIG. 2.

The liposomes of the present invention possess certain attributes which make them particularly suited for delivering the porphyrin photosensitizers. Conventional liposomal formulations are preferentially taken up by the reticuloendothelial system (RES) organs such as the liver and spleen. When this occurs, the major portion of the liposomal encapsulated water insoluble drug is not available to tumor sites since it is localized in the RES. In contrast, the liposomes formed in the present invention are "fast breaking" in that the drug-liposome combination is stable in vitro but when administered in vivo, the photosensitizer is rapidly released into the bloodstream where it associates with serum lipoproteins. It is believed that this inhibits the drug from being accumulated in non-target tissues such as the liver, where liposomes otherwise have a tendency to concentrate. The "fast breaking" nature of the present liposomes may be due to the manner in which the porphyrin photosensitizer associates with the lipid bilayer of the liposomes of the present invention.

In addition, the particular combination of a disaccharide or polysaccharide and one or more phospholipids forms a liposomal formulation which gives liposomes which exhibit excellent reproducibility in terms of particle size. Reproducibility and narrow particle size distribution of the liposomal solution upon reconstitution with water is enhanced by an increased speed of hydration since a delay in hydration results in larger liposomes or precipitation of the drug. The addition of the disaccharide or polysaccharide provides instantaneous hydration and the largest surface area for depositing a thin film of the drug-phospholipid complex. This thin film provides for faster hydration so that when the liposome is formed by adding the aqueous phase, the liposomes formed are of sufficiently small and uniform particle size such that the composition can be sterile filtered without any pre-filtering or separation of components with larger particle size. This provides significant advantages in terms of manufacturing ease. In addition, the present liposomes provide 80–100% encapsulations of a drug which is expensive and requires a complicated synthetic procedure to produce. Thus, there is no reworking necessary and very little waste of the drug.

Disaccharides or polysaccharides are preferred to monosaccharides. To keep the osmotic pressure of the liposome formulation similar to blood, no more than 4–5% monosaccharides can be added. In contrast, the same osmotic pressure can be generated with 9–10% of a disaccharide. This higher amount of disaccharide provides for the larger surface area which leads to the smaller particle size when the lyophilyzed liposomes are reconstituted.

The preferred liposomal formulation of the present invention for incorporation of porphyrin photosensitizers comprise a disaccharide or polysaccharide, and one or more phospholipids which may be a phosphatidyl choline and a phosphatidyl glycerol. The disaccharide or polysaccharide are preferably chosen from lactose, trehalose, maltose, maltotriose, palatinose, lactulose or sucrose.

The preferable phospholipids are phosphatidyl cholines such as dimyristoyl phosphatidyl choline (DMPC), phosphatidyl choline (PC), dipalmitoylphosphatidy choline (DPPC), distearoylphosphatidyl choline (DSPC), soy phosphatidyl choline or egg phosphatidyl choline. The preferable phosphatidyl glycerols are dimyristoylphosphatidylglycerol (DMPG), and egg phosphatidylglycerol (EPG). Other phospholipids that may be incorporated in the liposomes of the present invention are phosphatidyl ethanolamine, phosphatidic acid, phosphatidylserine and phosphatidylinositol. More preferably the liposomes comprise lactose, dimyristoylphosphatidyl choline (DMPC) and egg phosphatidylglycerol (EPG). The disaccharide or polysaccharide and phospholipid are formulated in a preferred ratio of about 10–20 to 0.5–6, respectively, most preferably 10 to 1.5–4.0.

BRIEF DESCRIPTION OF THE DRAWINGS

Other objects, features and advantages will occur from the following descriptions of preferred embodiments and the accompanying drawings in which.

DETAILED DESCRIPTION OF THE INVENTION

Figure 1:
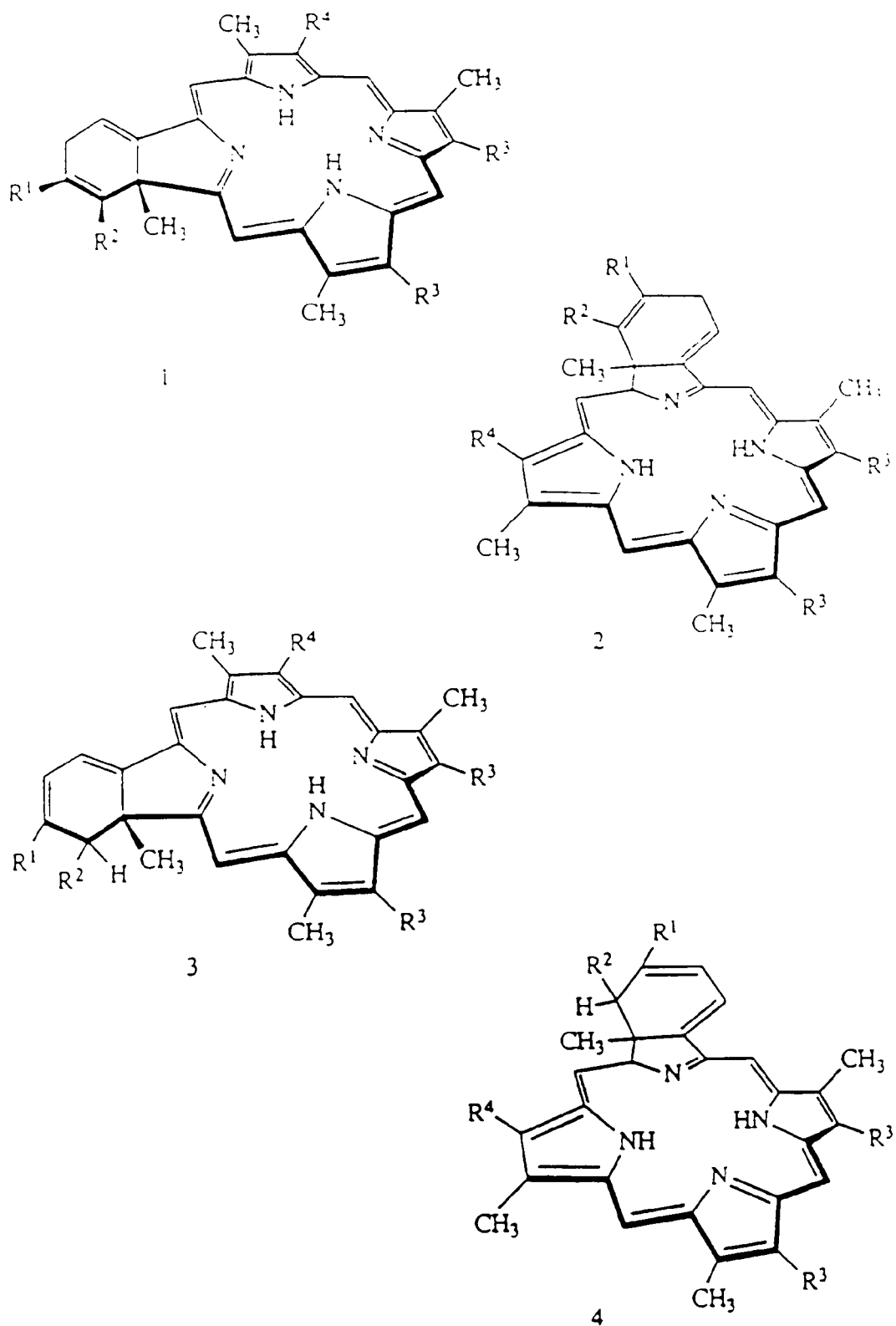
FIG. 1 shows the structure of green porphyrin (Gp) compounds used in the liposomal formulations of the invention.

The present invention relates to a pharmaceutical liposome formulation of a porphyrin photosensitizer for use in the photodynamic therapy or diagnosis of tumors, or for a variety of other therapeutic applications. The liposomes are formed upon addition of an aqueous vehicle to a freeze-dried formulation of a porphyrin photosensitizer, a disaccharide or polysaccharide, and one or more phospholipids such as phosphatidyl cholines or phosphatidyl glycerols. The presence of the disaccharide or polysaccharide in the formulation yields liposomes which have extremely small and narrow particle size, in which the porphyrin photosensitizers may be stably incorporated into the liposome in an efficient manner with encapsulation efficiency approaching 80–100% of the drug. The liposomes exhibit physical and chemical stability such that they retain incorporated porphyrin drugs without leakage upon prolonged storage, as either a reconstituted liposomal suspension or cryodesiccated powder. For example, BPD-MA, a preferred porphyrin photosensitizer, maintained its potency in the cryodesiccated liposome formulation for a period of at least nine months at room temperature and had a projected shelf life of at least two years.

The class of porphyrin photosensitizers preferably utilized in the present invention are the hydro-monobenzoporphyrins (GP) disclosed in U.S. Pat. Nos. 4,920,143 and 4,883,790, and most preferably the compounds designated benzoporphyrin derivative (BPD), particularly BPD-MA having the formula set forth in FIG. 2.

Liposomes containing a selected porphyrin photosensitizer as described herein may be prepared by dissolving the porphyrin photosensitizer, the phospholipids and other optional adjuvants such as antioxidants in methylene chloride or other suitable organic solvents. The resulting solution is dried under vacuum until the organic solvent is evaporated. The solid residue is dispersed in an aqueous solution of the disaccharide or polysaccharide and homogenized. The solution is then freeze dried for storage and reconstituted prior to administration with a suitable aqueous vehicle such as sterile water for injection. Upon reconstitution, liposomes are formed which incorporate a therapeutically effective amount of the porphyrin photosensitizer.

The liposomal formulation of the present invention provides liposomes of sufficiently small and narrow particle size such that it can be manufactured without filtering to separate off larger particles or utilizing other mechanical methods of obtaining a narrow distribution of particle size.

As noted, the preferred phospholipids are the phosphatidyl cholines such as dimyristoyl phosphatidyl choline (DMPC), phosphatidyl choline (PC), dipalmitoyl-phosphatidyl choline (DPPC) and distearoylphosphatidyl choline (DSPC) with DMPC being preferred. The preferred phosphatidyl glycerols are dimyristoyl phosphatidylglycerol (DMPG) and egg phosphatidyl-glycerol (EPG) with DMPG being preferred. The preferred disaccharides or polysaccharides are lactose, trehalose, maltose, maltotriose, palatinose, lactulose or sucrose with lactose or trehalose being most preferred. The disaccharide and phospholipids are formulated in a preferred ratio of about 10–20 to 0.5–6 respectively, most preferably 10 to 1.5–4.0.

A preferable but not limiting formulation is lactose or trehalose, dimyristoyl phosphatidyl choline and egg phosphatidyl glycerol in a concentration ratio of 10 to 0.94–1.88 to 0.65–1.30, respectively.

Other optional ingredients in the liposomal formulation are antioxidants such as butylated hydroxytoluene, α-tocopherol and ascorbyl palmitate.

The use of these porphyrin photosensitizers incorporated in liposomes for the treatment or diagnosis of cancer is described herein as a new effective treatment or therapeutic method. The liposomal formulations are useful in sensitizing neoplastic cells or other abnormal tissue including infectious agents to destruction by exposure to light using preferably, visible light. Upon photoactivation, the porphyrin photosensitizer promote the formation of singlet oxygen which is responsible for the cytotoxic effect. In addition, the porphyrin photosensitizers, when photoactivated, will fluoresce when subjected to appropriate excitation wavelengths. This fluorescence can be used to localize the tumor or other target tissue. By incorporating the porphyrin photosensitizer in the liposomes of the present invention, more efficient sensitization of tumor tissues can be obtained.

Generally speaking, the concentration of the porphyrin photosensitizer in the liposome depends upon the nature of the photosensitizer used. When the benzoporphyrin derivatives such as BPD-MA are used, the photosensitizer is incorporated in the liposomes at a concentration of about 0.10% up to 0.5% w/v, yielding a reconstituted solution of up to 5.0 mg/ml.

Such liposomes are typically administered parenterally. Injection may be intravenous, subcutaneous, intramuscular, intrathecal, or even intraperitoneal. The liposomes could be administered by aerosol intranasaly or intrapulmonarily. The freeze dried powder may be packed in vials for reconstitution with sterile water prior to injection. Of course, these compositions may also contain minor amounts of nontoxic, auxiliary substances such as pH buffering agents and the like.

The quantity of photosensitizer liposome formulations to be administered depends on the choice of active ingredients, the conditions to be treated, the mode of administration, the individual subject and the judgement of the practitioner. Generally speaking, dosages in the range of 0.05–10 mg/kg may be needed. The foregoing range is of course merely suggestive, as the number of variables in regard to an individual treatment regime is large and considerable excursions from these recommended values are expected.

For use as a diagnostic in localizing tumor tissue or in localizing atherosclerotic plaques, the compounds or conjugates of the invention are administered systemically in the same general manner as is known with respect to photodynamic therapy. The waiting period to allow the drugs to clear from tissues to which they do not accumulate is approximately the same, about 30 minutes to 10 hours. After the compounds of the invention or their conjugates have been permitted to localize, the location of the target tissue is determined by detecting the presence of the drug.

For diagnosis, the compounds incorporated in the liposomes may be used along with, or may be labeled with, a radioisotope or other detecting means. If this is the case, the detection means depends on the nature of the label. Scintigraphic labels such as technetium or indium can be determined using ex vivo scanners. Specific fluorescent labels can also be used, but these require prior irradiation, as does the detection based on fluorescence of the compounds of the invention themselves.

For activation of the photosensitizer of the invention, any suitable absorption wavelength is used. This can be supplied using the various methods known to the art for mediating cytotoxicity or fluorescence emission, such as visible radiation, including incandescent or fluorescent light sources or photodiodes, such as light emitting diodes. Laser light is also used for in situ delivery of light to the localized photosensitizer In a typical protocol, several hours before irradiation, approximately 0.5–1.5 mg/kg of the green porphyrin is injected intravenously and then excited by an appropriate wavelength.

The methods of preparation of liposomal porphyrins of the present invention and photodynamic treatment therewith described in the Examples contained later herein are readily adapted to the production and use of analogously described liposomes by simple substitutions of appropriate porphyrins, phospholipids or methods.

Either unilamellar or multilamellar or other types of liposomes may be used in the practice of the present invention. They may be prepared in a suspension form or may be formed upon reconstitution of a lyophilized powder containing the porphyrin-phospholipid-saccharide composition with an aqueous solution.

These following examples are presented to describe preferred embodiments, utilities and attributes of the present invention but are not meant to limit the invention. For example, although DMPC and EPG were used to form liposomes, these particular phospholipids are by no means the only available usable lipid forms known to those skilled in the art. Nor do the particular methods of forming or preparing the liposomes described herein constitute the only methods for preparing liposomes contemplated by the present invention. Moreover, although the examples imply the photosensitizer BPD-MA, the procedures, results and preparations should be similar for other porphyrin photosensitizers.

EXAMPLE 1

Preparation of Liposomes Containing BPD-MA

BPD-MA was synthesized as described in U.S. Pat. Nos. 4,920,143 and 4,883,790, incorporated herein by reference. Liposomes were prepared according to the following general procedure:

BPD-MA, butylated hydroxytoluene, ascorbyl palmitate and the phospholipids are dissolved in methylene chloride and the solution is filtered through a 0.22 micron filter. The solution is then dried under vacuum using a rotary evaporator until the methylene chloride level in the solid residue is not detectable by gas chromatography. A 10% lactose/water for injection solution is then prepared and filtered through a 0.22 micron filter. The lactose/water solution is warmed to about 35° C. and added to the flask containing the solid residue of the photosensitizer/phospholipid. The solid residue is dispersed in the 10% lactose/water solution and stirred for about one hour, cooled, and passed through a homogenizer. The solution is then filtered through a 0.22 micron Durapore® hydrophilic filter. Optionally, the solution may first be prefiltered with a 5.0 micron prefilter. The filtrate is collected, filled into vials and freeze dried and stored under refrigeration. The freeze dried composition is reconstituted with water for injection prior to administration.

Using the foregoing procedure, several different preparations of the BPD-MA liposomal composition were prepared as follows:

EXAMPLE 1A

Preparation of a Liposomal Drug Delivery System Containing BPD-MA up to 4.0 mg/ml

| Ingredient | Amount % w/v |
| --- | --- |
| BPD-MA | 0.2 to 0.4 |
| Dimyristoyl Phosphatidyl Choline | 0.94 to 1.88 |
| Egg Phosphatidyl Glycerol | 0.65 to 1.30 |
| Lactose or Trehalose | 8.0 to 12.0 |
| Ascorbyl Palmitate | 0.002 to 0.004 |
| Butylated Hydroxy Toluene | 0.0002 to 0.0004 |
| Water for Injection | Q.S. |

EXAMPLE 1B

Preparation of a Liposomal Drug Delivery System Containing BPD-MA up to 3.0 mg/ml

| Ingredient | Amount % w/v |
| --- | --- |
| BPD-MA | 0.2 to 0.3 |
| Dimyristoyl Phosphatidyl Choline | 1.7 to 2.6 |
| Soy Phosphatidyl Choline | 2.3 to 3.5 |
| Lactose or Trehalose | 8.0 to 12.0 |
| Ascorbyl Palmitate | 0.002 to 0.003 |
| Butylated Hydroxy Toluene | 0.0002 to 0.0003 |
| Water for Injection | Q.S. |

EXAMPLE 1C

Preparation of a Liposomal Drug Delivery System Containing BPD-MA up to 5.0 mg/ml

| Ingredient | Amount % w/v |
| --- | --- |
| BPD-MA | 0.2 to 0.5 |
| Phosphatidyl Ethanolamine | 1.0 to 2.5 |
| Egg Phosphatidyl Choline | 0.7 to 1.75 |
| Lactose or Trehalose | 8.0 to 12.0 |
| Ascorbyl Palmitate | 0.002 to 0.005 |
| Butylated Hydroxy Toluene | 0.0002 to 0.0005 |
| Water for Injection | Q.S. |

EXAMPLE 1D

Preparation of a Liposomal Drug Delivery System Containing BPD-MA up to 4.0 mg/ml

| Ingredient | Amount % w/v |
| --- | --- |
| BPD-MA | 0.2 to 0.4 |
| Dimyristoyl Phosphatidyl Choline | 1.13 to 2.26 |
| Phosphatidic Acid | 0.43 to 0.86 |
| Lactose or Trehalose | 8.0 to 12.0 |
| Ascorbyl Palmitate | 0.002 to 0.004 |
| Butylated Hydroxy Toluene | 0.0002 to 0.0004 |
| Water for Injection | Q.S. |

EXAMPLE 1E

Preparation of a Liposomal Drug Delivery System Containing BPD-MA up to 1.0 mg/ml

| Ingredient | Amount % w/v |
| --- | --- |
| BPD-MA | 0.1 |
| Egg Phosphatidyl Choline | 0.55 |
| Egg Phosphatidyl Glycerol | 0.32 |
| Lactose | 8.0 to 12.0 |
| Ascorbyl Palmitate | 0.002 |
| Butylated Hydroxy Toluene | 0.0002 |
| Water for Injection | Q.S. |

EXAMPLE 1F

| Ingredient | Amount % w/v |
| --- | --- |
| BPD-MA | 0.2 to 0.3 |
| Dimyristoyl Phosphatidyl Choline | 1.1 to 1.6 |
| Phosphatidic Acid | 0.4 to 0.7 |
| Lactose or Trehalose | 8.0 to 12.0 |
| Ascorbyl Palmitate | 0.002 to 0.005 |
| Butylated Hydroxy Toluene | 0.0002 to 0.0005 |
| Water for Injection | Q.S. |

EXAMPLE 2

Physical and Chemical Stability of Liposomal BPD-MA

The physical stability of the liposomal BPD-MA was assessed by monitoring the particle size distribution and osmolarity of the reconstituted solution over time when stored at various temperatures. In all cases the mean particle size distribution was less than 200 nm. Osmolarity also showed no significant difference. The results are shown in Table 1. The data supports the physical stability of this dosage form.

TABLE I

Stability of Liposomal BPD-MA for Injection 25 mg/vial

| | Mean Particle Size Distribution nm | Osmolarity mosm/kg |
|---|---|---|
| Initial | 170 | 295 |
| 3° C.-1 Month | 168 | 287 |
| 3° C.-3 Month | 157 | 291 |
| 3° C.-6 Month | 189 | 281 |
| 23° C.-1 Month | 147 | 308 |
| 23° C.-3 Month | 155 | 291 |
| 23° C.-6 Month | 172 | 285 |
| 30° C.-1 Month | 169 | 305 |
| 30° C.-3 Month | 134 | 291 |
| 30° C.-75% RH 1 Month | 155 | 287 |
| 30° C.-75% RH 3 Month | 132 | 294 |
| Light Cabinet 0.25 Month | | 300 |

The chemical stability of the constituted dosage form was followed by monitoring the potency, degradation products and pH of the reconstituted solution. The potency of the reconstituted parenteral dosage form was assessed by chromatography with potency calculated on as is basis. The potency of the cryodesiccated powder showed a slight change from initial up to six month period at 3 or 23° C. with data ranging from 100.0–98.2 percent of labeled claims. The results are shown in Table II.

TABLE II

Stability of Liposomal BPD-MA for Injection 25 mg/vial

| | Potency Assay BPD-MA mg/vial | Potency Assay BPD-MA 0/0 Label | Degradation Product HPLC Area 0/0 | pH |
|---|---|---|---|---|
| Initial | 25.1 | 100.4 | 0.82 | 6.8 |
| 3° C.-1 Month | 25.0 | 100.0 | 0.81 | 6.4 |
| 3° C.-3 Month | 25.1 | 100.4 | 0.72 | 6.4 |
| 3° C.-6 Month | 24.7 | 98.8 | 0.80 | 6.4 |
| 23° C.-1 Month | 25.3 | 101.2 | 0.83 | 6.4 |
| 23° C.-3 Month | 25.0 | 100.0 | 0.85 | 6.4 |
| 23° C.-6 Month | 24.7 | 98.6 | 0.80 | 6.2 |
| 30° C.-1 Month | 25.2 | 100.8 | 0.83 | 6.3 |
| 30° C.-3 Month | 25.1 | 100.2 | 0.85 | 6.3 |
| 30° C.-75% RH 1 Month | 25.2 | 100.8 | 0.80 | 6.3 |
| 30° C.-75% RH 3 Month | 24.6 | 98.4 | 0.80 | 6.3 |
| Light Cabinet 0.25 Month | 24.6 | 98.2 | 0.98 | 6.4 |

EXAMPLE 3

Distribution of Liposomal BPD-MA in Human Blood

The liposomal BPD-MA of the present invention was incubated in human blood for varying time periods and analyzed to determine the distribution of the drug to various blood compartments.

Table III shows the comparison of the distribution of liposomal $^{14}$C-BPD-MA (formulated) and $^{14}$C-BPD-MA in DMSO (non-formulated) between plasma and whole blood cells. $^{14}$C-BPD-MA at 25 μg/ml was incubated with whole blood at 4° C.

Table IV shows the distribution of liposomal $^{14}$C-BPD-MA in plasma after 1, 6 and 24 h incubation. Rudel's density gradient ultracentrifugation was used to obtain fractions. Radioactivity is expressed as a percentage of total radioactivity in the plasma (mean±S.D.) n=2).

Table V shows the distribution of $^{14}$C-BPD-MA in DMSO (expressed as % of total radioactivity) between human plasma fractions obtained by Rudel's density gradient centrifugation, following 1 and 24 h incubation. Each value represents mean±S.D. (n=3).

The results shown in the following Tables III, IV and V demonstrate the "fast breaking" nature of the liposomal formulation of the present invention. As shown above the active drug associates rapidly with the lipoprotein compartment of the blood which in turn acts as a circulating reservoir of the drug.

TABLE III

| | % of Total Counts | | | |
|---|---|---|---|---|
| | Plasma | | Red and White Blood Cells | |
| Time(h) | Liposomal | DMSO Solution | Liposomal | DMSO Solution |
| 1 | 86.3 | 92.5 | 13.7 | 7.5 |
| 6 | 94.1 | — | 5.9 | — |
| 24 | 88.7 | 84.0 | 11.3 | 16.0 |

TABLE IV

| Fraction | Composition | % of Total DPM | | |
|---|---|---|---|---|
| | | 1 h | 6 h | 24 h |
| 1 + 2 | lipoproteins | 91.1 ± 0.9 | 89.8 ± 0.9 | 90.4 ± 4.9 |
| 3 | salt & water | 1.8 ± 0.5 | 2.5 ± 0.4 | 0.9 ± 0.2 |
| 4 | albumin | 6.6 ± 0.1 | 5.3 ± 2.3 | 6.5 ± 0.1 |
| 5 | other proteins | 0.6 ± 0.2 | 2.6 ± 3.0 | 2.4 ± 2.2 |

TABLE V

| Fraction | Composition | % Total DPM | |
|---|---|---|---|
| | | 1 hour | 24 hours |
| 1 + 2 | lipoproteins | 49.1 ± 2.6 | 86.7 ± 2.2 |
| 3 | salt & water | 13.1 ± 2.0 | 7.41 ± 0.8 |
| 4 | albumin | 35.9 ± 0.1 | 4.9 ± 2.9 |
| 5 | other plasma proteins | 1.8 ± 1.0 | 1.1 ± 0.1 |

EXAMPLE 4

Antitumor Activity of Liposomal BPD-MA

Dose-response curves of liposomal benzoporphyrin derivative monoacid (BPD-MA) were obtained by exposing tumor-bearing mice treated with various doses of drug to 150 J/cm$^2$ of 690 nm laser light. The results indicated an $ED_{50}$ in the region of 1.5 mg/kg.

DBA/2 male mice carrying M1-S tumors were shaved and depilated at least 24 hours prior to treatment. Liposomal BPD-MA was injected i.v., and after a 3 hour waiting period, during which time the animals were kept in the dark, the tumor site was exposed to 150 J/cm$^2$ of 690 nm light from an argon ion pumped dye laser. The animals were then returned to the cage, and observed over the next 20 days.

| Dose Groups | Animals |
|---|---|
| BPD-MA 0 mg/kg | 2 × 10 |
| BPD-MA 0.5 mg/kg | 2 × 10 |
| BPD-MA 1.0 mg/kg | 2 × 10 |
| BPD-MA 1.5 mg/kg | 2 × 10 |
| BPD-MA 2.0 mg/kg | 2 × 10 |

Two series of experiments were carried out, each consisting of 5 groups of animals treated with 0, 0.5, 1.0, 1.5, or 2.0 mg/kg liposomal BPD-MA. (See Table VI)

100% of the animals at the 2 mg/kg dose point were tumor-free at day 7 in both series I and II. By day 14, 30% of the tumors recurred in series I, and 20% in series II, and by day 20, 60% of the mice were tumor positive in series I and 30% in series II.

At the 1.5 mg/kg point, 70% of the animals in series I and 80% in series II were tumor-free at Day 7, 30% in both series were tumor-free at Day 14, and 10% and 20% were tumor-free at Day 20.

The 1.0 mg/kg dose points in the two series were dissimilar in that 40% of the animals were tumor-free at day 7 in series I, 20% at day 14, and 10% at Day 20. In series II, 90% of the animals were tumor-free at day 7, 40% at day 14 and 30% at day 20.

No effect was noted at either the 0.5 mg/kg or the 0 mg/kg dose points. The tumors continued to grow at the normal rate.

The disparity between the two series at the 1.0 mg/kg dose point makes it difficult to determine an $ED_{50}$. However, at this time we can deduce that the $ED_{50}$ will lie in the region of 1.5 mg/kg.

The following Table VI provides the number of animals remaining tumor free at Day 7, 14 and 20 after treatment with varying doses of liposomal BPD-MA and 150 J/cm$^2$ 690 nm laser light.

TABLE VI

| | Drug Dose | # Animal | D7 | D14 | D20 |
|---|---|---|---|---|---|
| Series I | 0.0 mg/kg | 10 | 0 | — | — |
| | 0.5 mg/kg | 10 | 0 | — | — |
| | 1.0 mg/kg | 10 | 4 | 2 | 1 |
| | 1.5 mg/kg | 10 | 7 | 3 | 1 |
| | 2.0 mg/kg | 10 | 10 | 7 | 4 |
| Series II | 0.0 mg/kg | 10 | 0 | — | — |
| | 0.5 mg/kg | 10 | 0 | — | — |
| | 1.0 mg/kg | 10 | 9 | 4 | 3 |
| | 1.5 mg/kg | 10 | 8 | 3 | 2 |
| | 2.0 mg/kg | 10 | 10 | 8 | 7 |

We claim:

1. A liposomal formulation comprising liposomes that comprise phosphatidyl choline, phosphatidyl glycerol and a porphyrin macrocycle photosensitizer, wherein said liposomes have a mean particle size distribution of less than 200 nm.

2. The liposomal formulation of claim 1 in freeze-dried form.

3. The liposomal formulation of claim 1, wherein said sugars are selected from disaccharides or polysaccharides.

4. The liposomal formulation of claim 3 wherein said disaccharides are selected from lactose or trehalose.

5. The liposomal formulation of claim 1 wherein the lipid bilayer of said liposomes consists essentially of dimyristoyl phosphatidyl choline and egg phosphatidyl glycerol.

6. The liposomal formulation of claim 1 wherein said porphyrin macrocycle photosensitizer is a hydro-monobenzoporphyrin (Gp) of any one of the following formulas

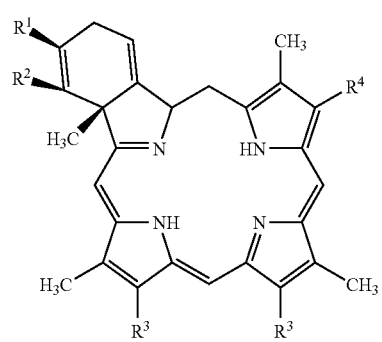

1

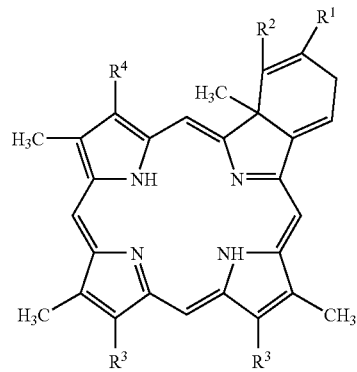

2

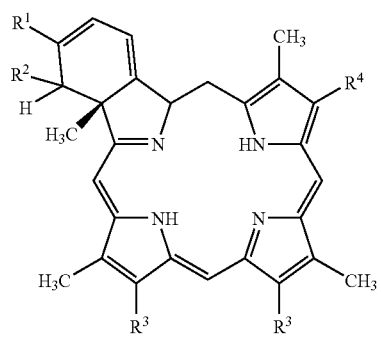

3

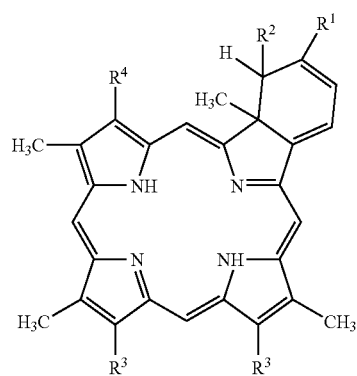

4

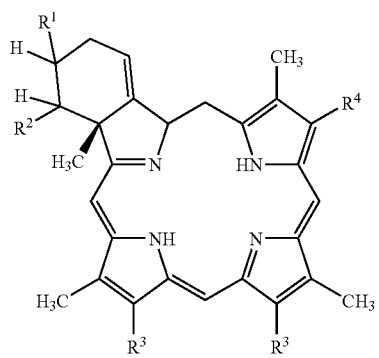

or

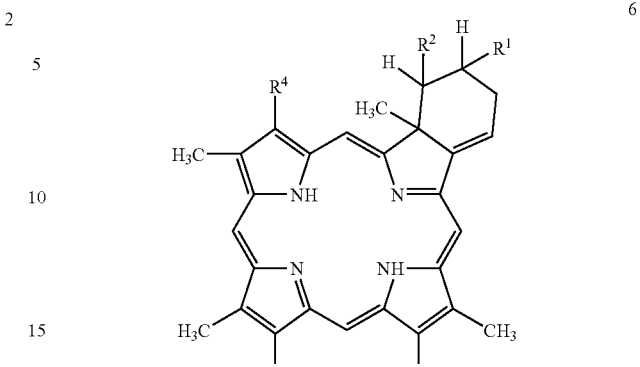

Figures 1, 2:
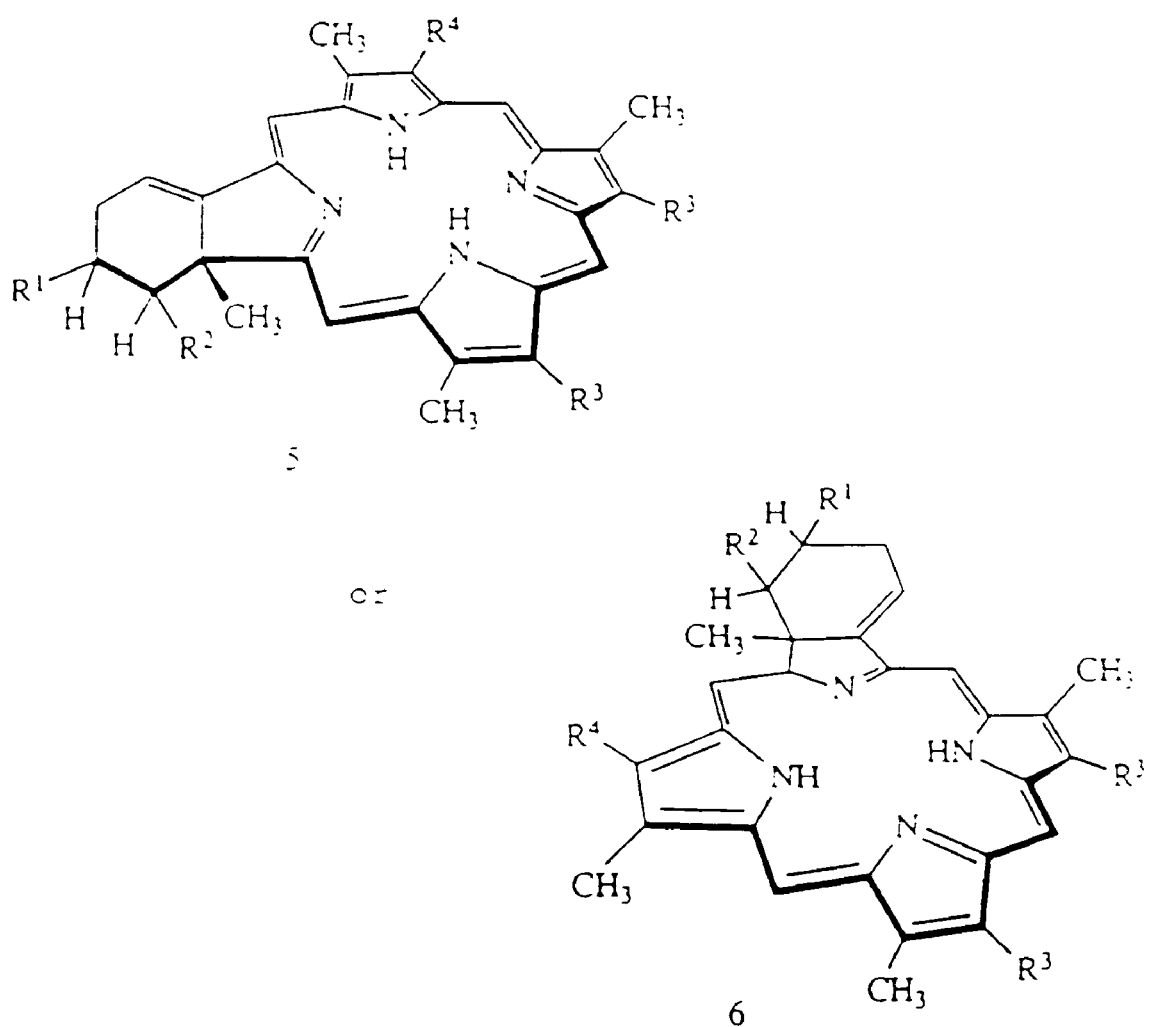
FIG. 2 shows the structure of four preferred forms of the hydro-monobenzoporphyrin derivatives of formulas 3 and 4 (BPDs).
Figure 2:
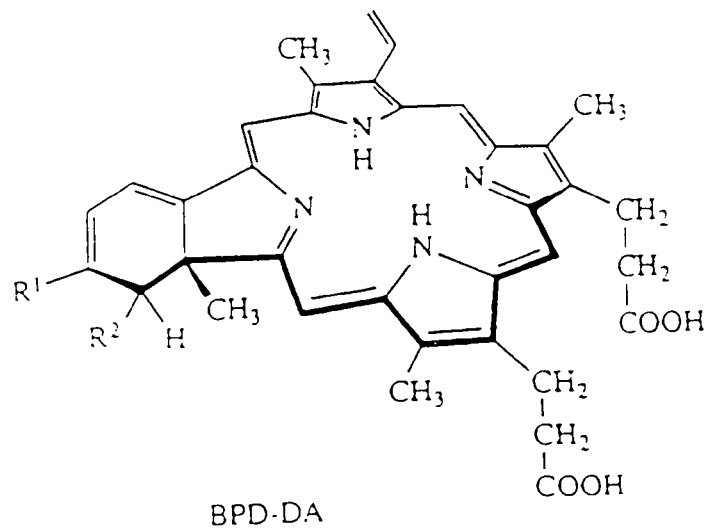
Figure 1:
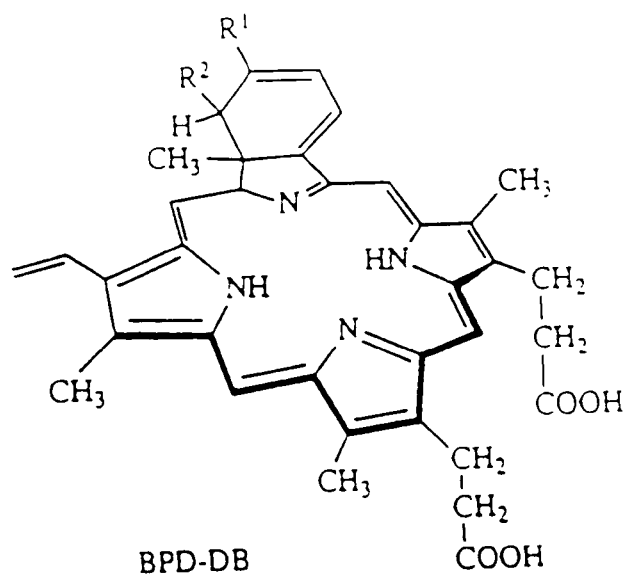
Figure 2:
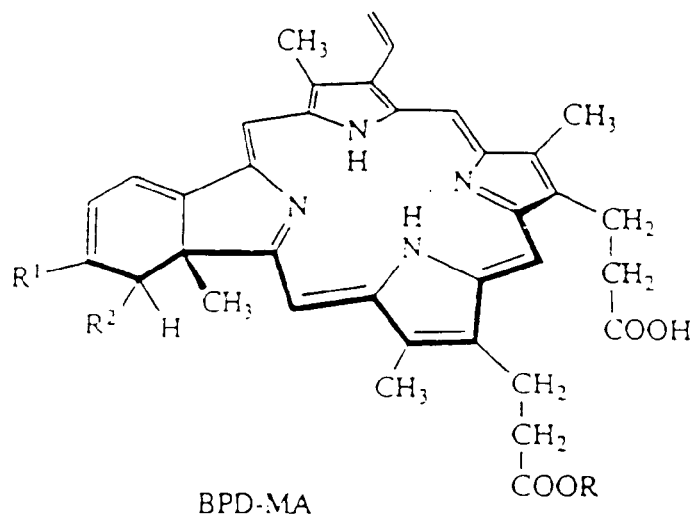
Figure 2:
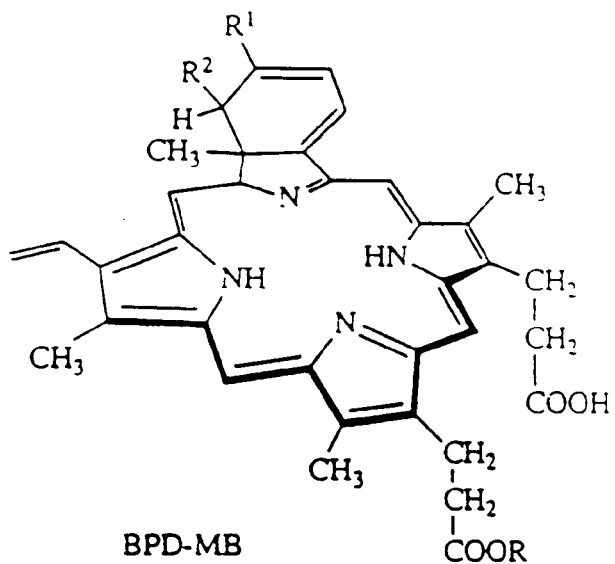

6 and having a light absorption maximum between 670–780 nm, mixtures thereof, and the metallated and labeled forms thereof, wherein each $R^1$ and $R^2$ is independently selected from the group consisting of carbalkoxy (2–6C), alkyl (1–6C) sulfonyl, aryl (6–10C) sulfonyl, aryl (6–10C); cyano; and —CONR$^5$CO— wherein $R^5$ is aryl (6–10C) or alkyl (1–6C);

each $R^3$ is independently carboxyalkyl (2–6C) or a salt, amide, ester or acylhydrazone thereof, or is alkyl (1–6C); and $R^4$ is —CH=CH$_2$, —CHOR$^{4'}$, —CHO, —COOR$^{4'}$, —CH(OR$^{4'}$)CH$_3$, —CH(OR$^{4'}$)CH$_2$OR$^{4'}$, —CH(SR$^{4'}$)CH$_3$, —CH(NR$^{4'}{}_2$)CH$_3$, —CH(CN)CH$_3$, —CH(COOR$^{4'}$)CH$_3$, —CH(OOCR$^{4'}$)CH$_3$, —CH(halo)CH$_3$, or —CH(halo)CH$_2$(halo), wherein $R^{4'}$ is H, alkyl (1–6C) optionally substituted with a hydrophilic substituent, an organic group of less than 12C resulting from direct or indirect derivatization of vinyl, or 1–3 tetrapyrrole-type nuclei of the formula —L—P wherein —L— is selected from the group consisting of:

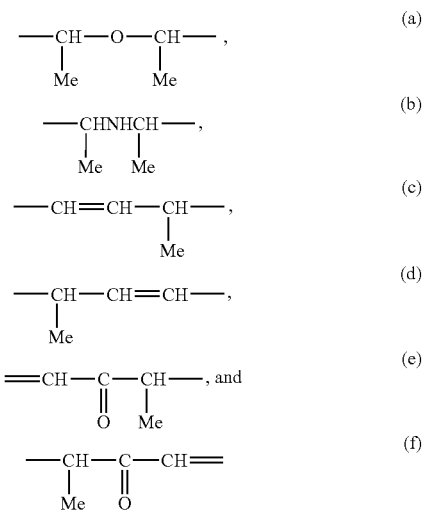

and P is selected from the group consisting of Gp which is of the formula of FIG. 1–2, but lacking $R_4$ and conjugated through the position shown as occupied by $R^4$ to L;

with the proviso that, if $R^4$ is —CH=CH$_2$, both $R^3$ groups cannot be carbalkoxyethyl.

7. The liposomal formulation of claim 6 wherein each $R^3$ is —CH$_2$CH$_2$COOH or salt, amide, ester or acylhydrazone thereof.

8. The liposomal formulation of claim 6 wherein each of $R^1$ and $R^2$ is carbalkoxy (2–6C).

9. The liposomal formulation of claim 7 wherein each of $R^1$ and $R^2$ is carbalkoxy (2–6C).

10. The liposomal formulation of claim 6 wherein said hydro-monobenzoporphyrin (Gp) is selected from the group consisting of:
BPD-DA wherein $R^1$ and $R^2$ thereof are carbomethoxy;
BPD-DB wherein $R^1$ and $R^2$ thereof are carbomethoxy;
BPD-MA wherein $R^1$ and $R^2$ thereof are carbomethoxy and R is methyl; and
BPD-MB wherein $R^1$ and $R^2$ thereof are carbomethoxy and R is methyl.

11. The liposomal formulation of claim 10 wherein said hydro-monobenzoporphyrin (Gp) is BPD-MA wherein $R^1$ and $R^2$ thereof are carbomethoxy and R is methyl.

12. The liposomal formulation of claim 5 wherein the amounts of photosensitizer, dimyristoyl phosphatidyl choline, and egg phosphatidyl glycerol in said liposomes are, relative to each other on a per weight basis, about 0.2 to 0.4 of porphyrin; 0.94 to 1.88 of dimyristoyl phosphatidyl choline; and 0.65 to 1.30 of egg phosphatidyl glycerol.

13. The liposomal formulation of claim 12 wherein the amount of sugar, relative to said amounts of photosensitizer, dimyristoyl phosphatidyl choline, and egg phosphatidyl glycerol in said liposomes on a per weight basis, is about 8.0 to 12.0 of sugar when said sugar is a disaccharide, or about half that amount if said sugar is a monosaccharide.

14. The liposomal formulation of claim 5 further comprising an antioxidant.

15. The liposomal formulation of claim 14 wherein said antioxidant is butylated hydroxytoluene or L-ascorbic acid 6-palmitate.

16. The liposomal formulation of claim 1 further comprising a pharmaceutically acceptable excipient.

17. A method of providing photodynamic therapy to a subject comprising
administering a formulation according to claim 1 to said subject wherein the porphyrin macrocycle photosensitizer, after release from said formulation, is capable of localizing to target tissues or cells, and
irradiating said tissues or cells at an appropriate wavelength of light after passage of sufficient time for said porphyrin macrocycle photosensitizer to localize.

18. A method of providing photodynamic therapy to a subject comprising administering a formulation according to claim 5 to said subject wherein the porphyrin macrocycle photosensitizer, after release from said formulation, is capable of localizing to target tissues or cells, and
irradiating said tissues or cells at an appropriate wavelength of light after passage of sufficient time for said porphyrin macrocycle photosensitizer to localize.

19. The liposomal formulation of claim 1 wherein the ratio of sugar to phospholipid is about 10–20 to 0.5–6.

20. The liposomal formulation of claim 19 wherein the ratio of sugar to phospholipid is 10 to 1.5–4.0.

21. The liposomal formulation of claim 1, wherein said liposomes are fast breaking and rapidly release the photosensitizer into the bloodstream to associate with lipoproteins upon in vivo administration.

22. The liposomal formulation of claim 1, wherein the osmolarity of said liposomes is that of human blood.

23. A pharmaceutical composition comprising the liposomal formulation of claim 1.

24. The liposomal formulation of claim 1, wherein said phosphatidyl choline is dimyristoyl phosphatidyl choline.

25. The liposomal formulation of claim 1, wherein said phosphatidyl glycerol is egg phosphatidyl glycerol.

26. The liposomal formulation of claim 1, wherein said liposomes further comprise one or more sugars.

* * * * *